United States Patent
Kopfer

[11] Patent Number: 5,823,980
[45] Date of Patent: Oct. 20, 1998

[54] COLLAPSIBLE TACTILE SUPPORT FOR BODY JOINTS

[76] Inventor: Rudolph J. Kopfer, 131 Sage Rd., Hulen Meadows, Ketchum, Id. 83340

[21] Appl. No.: 717,178

[22] Filed: Sep. 20, 1996

[51] Int. Cl.[6] .................................................. A61F 5/00
[52] U.S. Cl. ................... 602/21; 602/22; 473/276; 473/213
[58] Field of Search .................. 602/5, 6, 12, 16, 602/21, 22, 30; 601/23, 33, 40; 2/910, 161.1, 162, 163, 164; 128/878–880; 473/266, 269, 276, 207, 212, 213

[56] References Cited

U.S. PATENT DOCUMENTS

| | | |
|---|---|---|
| 1,469,315 | 10/1923 | Hansard . |
| 1,847,973 | 3/1932 | Morton .................................. 602/30 X |
| 3,680,869 | 8/1972 | Brady . |
| 3,985,364 | 10/1976 | Brady . |
| 4,176,839 | 12/1979 | Pinkus ..................................... 602/64 |
| 4,222,569 | 9/1980 | DeMascolo . |
| 4,241,922 | 12/1980 | Elliott, Jr. . |
| 4,384,571 | 5/1983 | Nazzo et al. ........................... 602/22 |
| 4,657,251 | 4/1987 | Larsen . |
| 4,765,320 | 8/1988 | Lindemann et al. ................... 602/22 |
| 4,781,178 | 11/1988 | Gordon ................................... 602/22 |
| 5,113,849 | 5/1992 | Kuiken et al. ...................... 602/21 X |
| 5,116,057 | 5/1992 | Mangiaracina . |
| 5,158,298 | 10/1992 | Goins . |
| 5,174,575 | 12/1992 | Leith et al. . |
| 5,183,458 | 2/1993 | Marx .................................... 602/30 X |
| 5,207,430 | 5/1993 | Goins . |
| 5,221,089 | 6/1993 | Barrett . |
| 5,346,462 | 9/1994 | Barber ................................ 602/30 X |
| 5,356,371 | 10/1994 | Hubbard ................................. 602/22 |
| 5,375,843 | 12/1994 | Johnston . |
| 5,401,017 | 3/1995 | McDonald et al. . |
| 5,466,215 | 11/1995 | Lair et al. .......................... 128/878 X |
| 5,476,439 | 12/1995 | Robinson ........................... 602/22 X |
| 5,499,820 | 3/1996 | Albertsson . |

FOREIGN PATENT DOCUMENTS

| | | | |
|---|---|---|---|
| 4218594 | 12/1993 | Germany ............................... 602/22 |
| 291995 | 6/1928 | United Kingdom ................... 602/30 |

OTHER PUBLICATIONS

Zimmer Catalogue p. 92, Fracture Appliances, "Fasler Finger Splint".

*Primary Examiner*—Linda C. Dvorak
*Attorney, Agent, or Firm*—Medlen & Carroll, LLP

[57] ABSTRACT

The present invention provides a collapsible tactile joint support for therapeutic use or as a training aid for sports. The collapsible tactile joint support of the present invention provides corrective tension for the joint up to a predetermined threshold level that is reached by applying an internal or external force, at which point the joint support bends or collapses thereby releasing the corrective tension and freeing movement in the joint. A collapsible tactile wrist support for use as a golf training aid is also described.

21 Claims, 4 Drawing Sheets

COLLAPSIBLE TACTILE SUPPORT FOR BODY JOINTS

FIELD OF THE INVENTION

The present invention relates generally to the field of support devices for body joints. More particularly, the present invention relates to collapsible joint supports useful as training aids for sports.

BACKGROUND OF THE INVENTION

Joint supports have found advantageous use not only in traditional therapeutic and occupational endeavors but also in the realm of training aids for golf, baseball, tennis and the like. These training aids typically take the form of rigid or substantially rigid support members designed to maintain a predetermined alignment of a joint.

For example, it is a well-known fact that the proper alignment of the wrists and forearms when swinging a baseball bat or golf club is critical for the proper transfer of mechanical energy at the point of impact with the ball. Thus, golfers are typically instructed that the back of the wrist of the leading hand (i.e. the left hand of a right-handed golfer) should be maintained in a coplanar arrangement relative to the back of the forearm during the swinging motion, to prevent a misalignment of the club face relative to the golf ball. Unfortunately, many golfers may unwittingly bend their wrist at the top of their backswing, resulting in a slice or hook due to the "open" or "closed" alignment of the club face at the point of impact. Another common problem occurs in the downswing, where the golfer can cock their wrist by "casting" the club or by overriding the left arm "pull through" with the right arm, again opening the club face prior to impact and causing a slice.

A multitude of prior art devices have been proposed to correct for the natural tendency of golfers to cock their wrists during their swing, including various types of rigid braces and molded housings designed to hold the wrist and forearm in proper alignment. See, e.g., U.S. Pat. Nos. 5,158,298 and 5,401,017. However, the elaborate and unwieldy construction of these prior art training aids renders them far too awkward and cumbersome for continuous use, particularly during a long round of golf on a hot summer day. It is also rather undesirable to play a round of golf at the local country club with a cast-like training aid strapped to one's arm, given the often important social and business aspects of the game. Generally, the prior art devices are user unfriendly.

More importantly, from a physical standpoint the stiffness and rigidity inherent in these devices is inappropriate for a full golf swing, which requires at least some up and down movement of the wrist relative to the forearm during the follow-through. Thus, even less obtrusive embodiments of these rigid support devices, such as that described in U.S. Pat. No. 1,469,315, can create substantial physical problems with repeated use, including soreness in the joint and possibly tendon or ligament damage. The provision of a uniform, substantially rigid support also fails to accommodate the individual needs of different golfers, who will necessarily require different levels of wrist support depending on their personal wrist strength and skill level.

An alternative approach has been to provide an audible signaling device incorporated into a golf glove, such as that disclosed in U.S. Pat. No. 4,222,569. Unfortunately, this device approaches the problem from the other extreme, in that it is not designed to provide any support for the wrist during the swinging motion to counteract the golfer's natural tendency to cock the wrist. Thus, with this device the emission of an audible signal simply notifies the golfer of the problem, without providing any physical assistance to correct it.

Thus, there remains a substantial need in the art for a training aid which will provide the requisite corrective support without completely inhibiting the flexion and extension of the joint. Such a device would ideally accommodate a user's individual characteristics, and be relatively unobtrusive as well as easy to attach and remove. Finally, such a device should also be readily adaptable for use in a variety of configurations for different joints of the body.

SUMMARY OF THE INVENTION

Accordingly, it is an object of the present invention to remedy the disadvantages encountered in the prior art, through the provision of a collapsible support which can be used both as a training aid for sports and for therapeutic rehabilitation of injured joints. The collapsible support of the present invention substantially improves over the prior art by enabling a tactile biofeedback mechanism to releasably restrain the user from moving a joint past a predetermined point, and by alerting the user once an internal or external force has been applied to the joint sufficient to exceed the desired strength of the support. Moreover, the collapsible tactile support of the present invention can be readily altered to accommodate an individual user's needs, including the relative strength of the joint itself and the desired level of stiffness in view of the particular sport and skill level.

Other and further objects, features, advantages and embodiments of the present invention will become apparent to one skilled in the art from reading the detailed description of the invention together with the drawings.

DESCRIPTION OF THE INVENTION

The collapsible tactile support of the present invention solves the problems in the prior art through the provision of a flexible or collapsible support member incorporated into a suitable attachment means. It is contemplated that the attachment means of the present invention can be easily configured for any joint and/or use, such as a golf trainer, and further that the collapsible support member can be constructed with varying degrees of strength resistance. It is further contemplated that support members of varying resistance will be fully interchangeable in the attachment means, thereby accommodating the specific needs of the individual user.

Thus, the present invention provides a collapsible joint support that can be universally configured and utilized as needed for a particular joint and sport. In a preferred embodiment, the collapsible joint support is configured as a golf training device. In a particularly preferred embodiment, the present invention provides a collapsible wrist support designed to releasably maintain the leading wrist of a golfer in a coplanar alignment with the back of the forearm during the backswing and follow-through of a golf club. As is evident from a review of the drawings and the detailed description provided below, this preferred embodiment represents a considerable improvement over prior art training aids, including devices such as that described in U.S. Pat. No. 5,499,820.

The '820 patent, although discussing the need to accommodate some movement in the following wrist during a golf swing, provides a largely ineffective configuration consisting of a substantially rigid brace attached to the wrist via a stretchable, resilient material. Unfortunately, the brace is also attached to both the forearm and the index finger with additional, non-resilient straps, creating at best a very limited and awkward up and down movement of the wrist at the substantial expense of comfort. In contrast, the collapsible support of the present invention provides for free movement of the wrist or other joint once a predetermined threshold force or pressure is applied sufficient to collapse the support member. Thus, the present invention releasably supports the joint in a corrective manner and provides tactile biofeedback to the user regarding the movement and position of the joint up to the desired threshold level, at which point the wrist or other joint is tactually released for free movement.

DETAILED DESCRIPTION OF THE PREFERRED EMBODIMENTS

Figure 1:
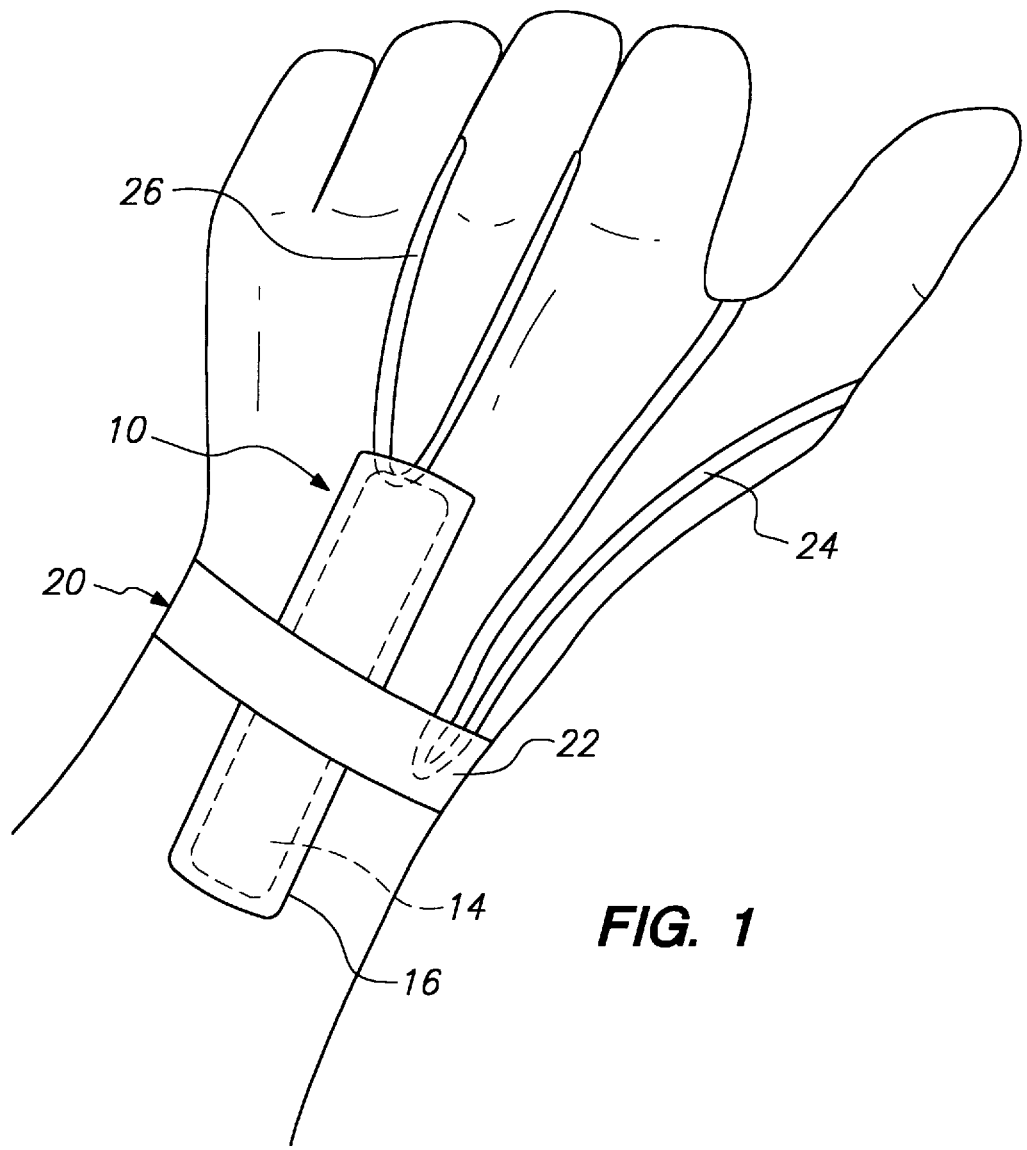
FIG. 1 is a perspective view of one embodiment of the collapsible support of the present invention configured for support of a user's wrist, with a strap and thumb and finger retention harnesses.

Referring to FIG. 1, the collapsible tactile support of the present invention comprises a collapsible support member (10) incorporated into a suitable means for positioning (20) the support member to support a joint. In the preferred embodiment shown in FIG. 1, the means for positioning (20) comprises at least one measurably adjustable strap (22) for securing the support member (10) over the bending point of the wrist or other joint. It is contemplated that the strap (22) can be advantageously made of nylon with a conventional tightening means such as an adjustable clip, or alternatively a VELCRO™ tab and closure mechanism. The strap (22) may be made measurably adjustable through any number of conventional means, such as suitable markings on the strap (22), to allow the user to measurably adjust the fit of the support member (10) and easily refasten at the desired level of tension. It is further contemplated that the strap (22) may be padded in a conventional fashion for the comfort of the user.

In an alternative embodiment, the means for positioning (20) the collapsible wrist support of the present invention further comprises a thumb retention harness (24) and/or a finger retention harness (26) for maintaining the proper positioning of the support member (10). It is contemplated that both retention harnesses can be advantageously constructed from either a substantially rigid material such as nylon cord, or alternatively a more elastic material such as rubber, and attached to the collapsible wrist support in a variety of ways. In the preferred embodiment shown in FIG. 1, the thumb retention harness (24) is attached to the strap (22), while the finger retention harness (26) is attached to the support member (10). It is further contemplated that either or both of these additional harnesses can be incorporated into the collapsible support of the present invention to more securely position the support member (10) on the wrist, as well as to enable its use with a conventional golf glove.

As shown in FIG. 1, in one embodiment the collapsible support member (10) of the present invention further comprises a support strip (14) enclosed within a cover (16) comprising, in one embodiment, a fabric material. It is also contemplated that additional padding material (not shown) can be interposed between the support strip (14) and the cover (16), for the comfort of the user. In an alternative embodiment, a block (not shown), such as a soft to semi-rigid elastic material such as rubber, can be placed between the wrist joint and support member (10) to control the degree of allowed wrist bend. Alternatively, the user can measurably adjust the strap (22) to provide varying degrees of allowed wrist bend prior to engagement of the wrist with the support member (10).

As can readily be recognized, tightening the support member (10) flush against the wrist will immediately engage the support member and releasably restrain any wrist movement. Conversely, loosening the strap or placing the block between the wrist joint and support member distances the support member (10) from the wrist, thereby allowing a limited amount of wrist movement prior to engagement by the support member (10). Thus, more experienced golfers who prefer a small amount of wrist movement during the backswing and follow-through can measurably adjust the strap (22) or insert a block to control the amount of wrist movement. In a particularly preferred embodiment described more fully below, the resistive or corrective tension of the support member (10) is further adjusted by variations in the collapse threshold of the support strip (14) itself.

Figure 2:
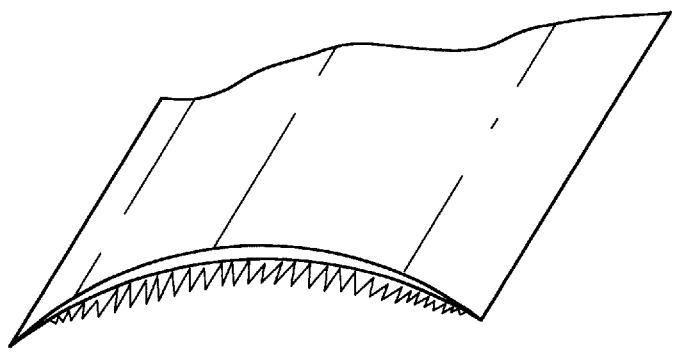
FIG. 2 is a perspective view of one embodiment of the support member of the present invention.

The support strip (14) comprises a generally rectangular strip of semi-rigid material such as, for example, spring steel, configured so as to "collapse" or bend at a point anywhere along the strip but always at that portion over the joint, and return to its original configuration when the collapsing pressure is removed. In the preferred embodiment illustrated in FIG. 2, the support strip (14) is slightly curved around a longitudinal axis, and is approximately 2–6 inches in length, 0.5 to 1.5 inches in width, and 0.003 to 0.005 inches thick. In a particularly preferred embodiment configured for most users, the support strip (14) is composed of spring steel with dimensions of 4 inches in length, 0.7 inches and slightly curved in width (0.75 flattened), and 0.004 inches thick.

Of course, many alternative geometrical configurations and dimensions of the support strip (14) can easily be made depending upon the particular joint to be supported (see, e.g., FIGS. 4 & 5) and the level of resistive or corrective support desired. For instance, an increase in the thickness, curvature or length of the support strip (14) will proportionately increase the "collapse threshold," or the level of resistance in the collapsible support member (10), thereby providing more corrective support for the user and increasing the amount of pressure required to "collapse" or bend the support member (10).

Thus, the resistance of the present invention can be varied to accommodate the skill level of the users by providing different support strips. By way of example, therefore, a beginning golfer may wish to select a support strip (14) having a relatively high resistance to bending (i.e. a high "collapse threshold"), while a more experienced golfer may desire a support strip (14) having a much lower resistance (i.e. a low "collapse threshold"). Such alternative embodiments of the support strip (14) are fully considered to be within the spirit and scope of the present invention.

Figure 3:
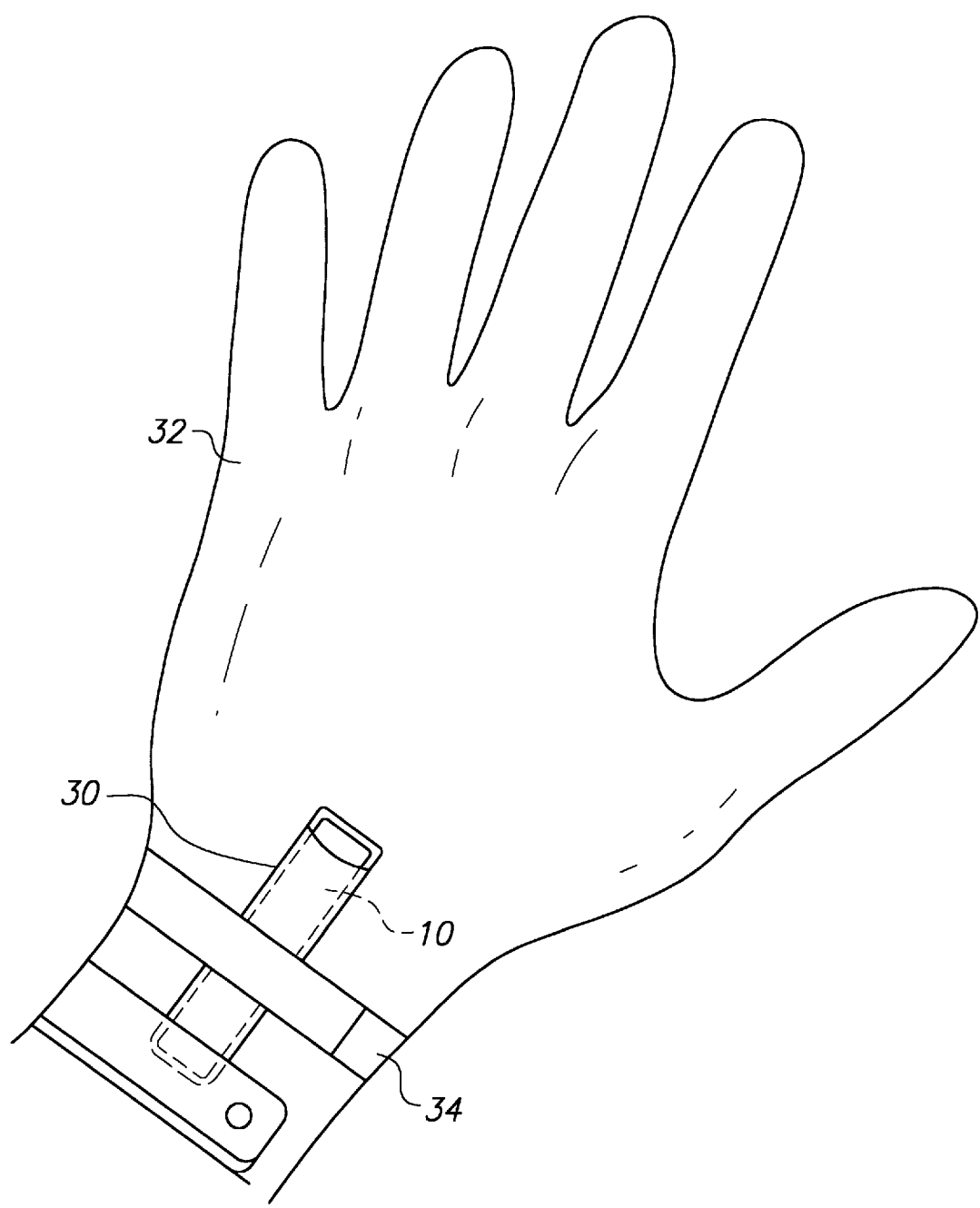
FIG. 3 is an alternative embodiment of the collapsible support of the present invention, incorporated into a golf glove.

Referring now to FIG. 3, in an alternative embodiment the collapsible support member (10) of the present invention is incorporated into a slip pocket (30) sewn into a conventional golf glove (32). In a particularly preferred embodiment, the slip pocket (30) further incorporates a tightening means (34) such as a tension-adjustable snap or, alternatively, a built-in strap controlled by a tension-adjustable VELCRO™ tab. The slip pocket (30) is positioned in the glove (32) such that the collapsible support member (10) is positioned over the back of the user's wrist where the hand bends at the forearm.

With this embodiment it is contemplated that support strips (14) of varying resistance levels as described above can easily be removed and replaced in the slip pocket (30) of the glove (32), so that a user can adjust the level of corrective support according to his or her own individual wrist strength and skill level. In addition, the tension can be adjusted via tightening means (34) to allow for limited wrist movement prior to engagement by the support member, as described previously.

By way of example, to use a device of this embodiment the user first inserts his or her hand into glove (32). The user then selects the support strip (14) providing the desired predetermined support and slides it into pocket (30), and tightens the glove and support member (10) to the desired tension against the wrist. When the wrist is maintained at the proper position, the support remains in its original position. If the user attempts to flex his or her wrist, but does not exert enough pressure against the support member (10) to overcome the collapse threshold, the support member (10) will aid in maintaining the correct position of the wrist. If the collapse threshold is exceeded by the continuous pressure exerted by the user, the support member (10) will collapse, delivering a tactile signal to the user to permit them to correct their wrist position. When the user's wrist is returned to the correct position, the support member (10) automatically snaps back (returns) to its original position supporting the wrist.

Thus, when used as a golf training aid, this device assists in training the golfer to position the wrist correctly throughout the entire swing; that is, to keep the wrist flat (or coplanar) relative to the back of the forearm during the backswing and downswing, and then subsequently "break" their wrist (i.e. receive the tactile signal from the present invention) well after ball contact at the end of the follow-through. It is further contemplated that in an alternative embodiment the collapsible wrist support of the present invention can deliver an audible signal in addition to the tactile signal.

Another advantageous use of the present invention for golf training purposes is the positioning of the support member (10) on the inside or outside of a golfer's ankle, to provide corrective support and tactile biofeedback to prevent the golfer from leaning or "falling" away from the desired direction of the ball flight during the backswing. The golfer's ankle typically bends outward in response to this leaning motion, which all too often results in either "topping" the ball or hitting the ball "fat"(i.e. striking the ground before striking the ball), since the club head is substantially displaced behind the ball at the bottom of the downswing. Thus, the present invention can also be used to provide corrective support to prevent the bending of the golfer's ankle (typically the right ankle on a right-handed golfer and vice versa), in a manner very similar to the corrective support of the wrist described above.

Figure 4:
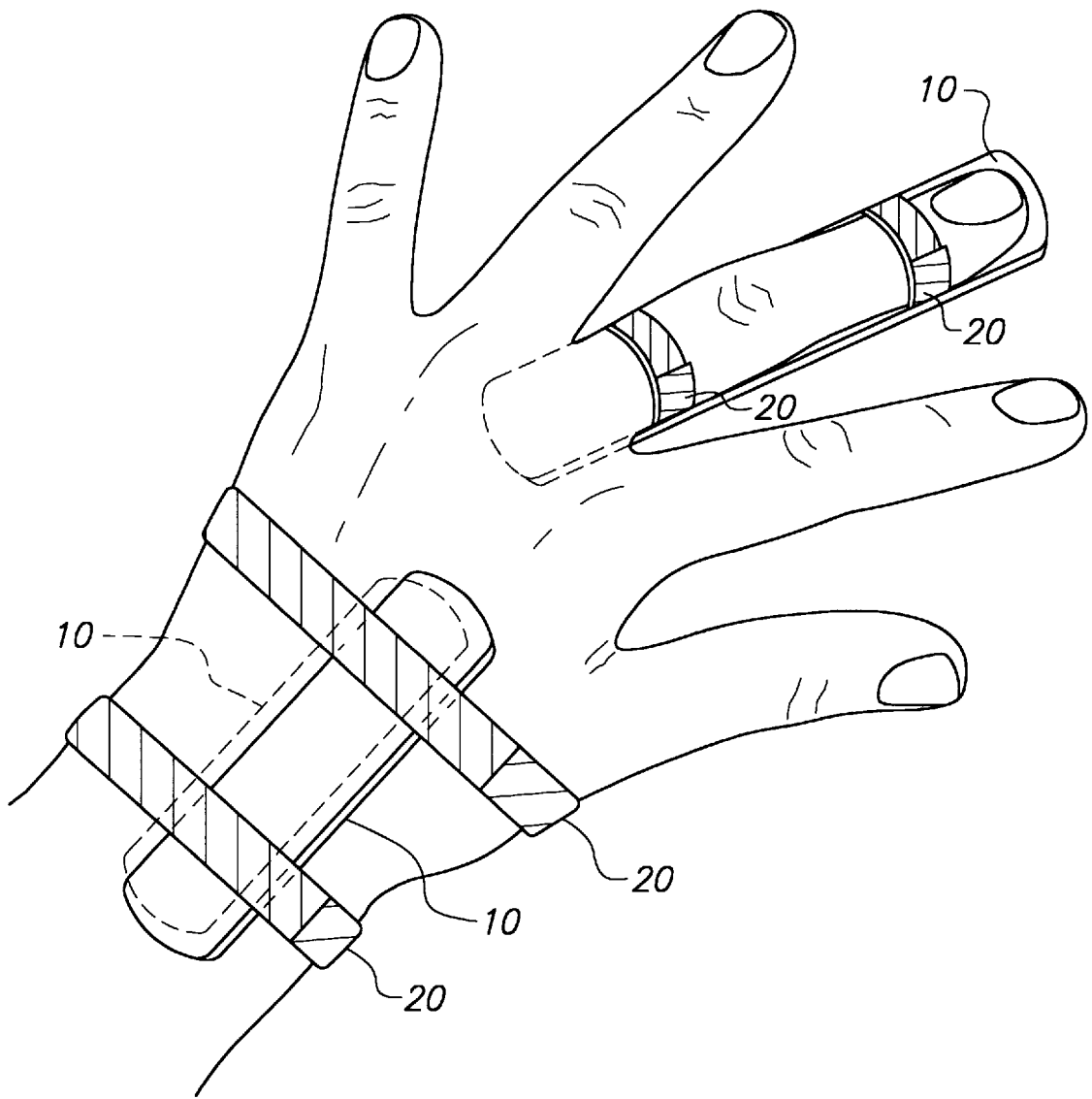
FIG. 4 illustrates a therapeutic use of the collapsible support of the present invention, releasably supporting an injured finger and wrist.
Figure 5:
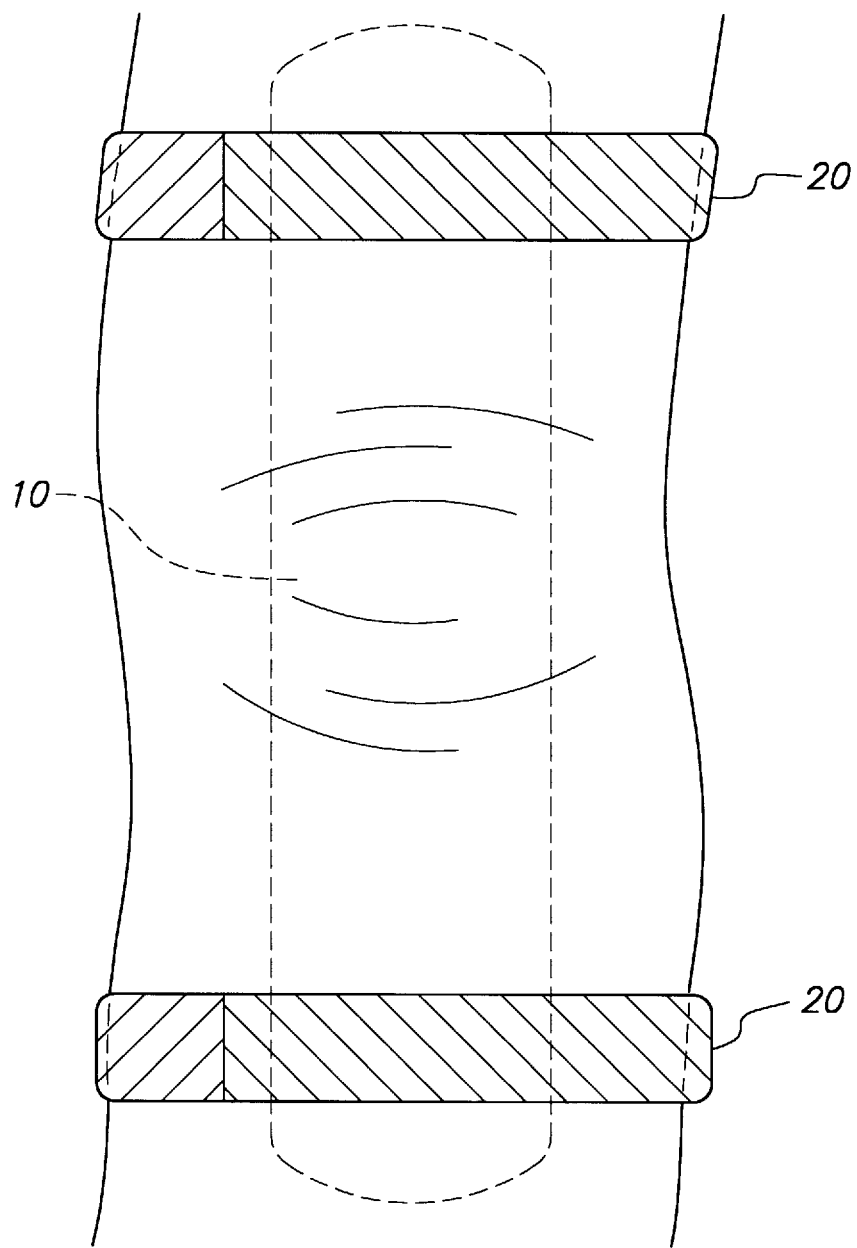
FIG. 5 illustrates another embodiment of the collapsible support of the present invention, configured for support of a user's knee.

The collapsible tactile support of the present invention may also find advantageous use for the therapeutic support and rehabilitation of injured joints. In one embodiment illustrated in FIG. 4, one support member (10) is positioned to releasably support a strained middle finger using, for example, VELCROT™ straps as positioning means (20). FIG. 4 also illustrates an alternative embodiment of the wrist support of the present invention, having two support members (10) positioned on either side of the wrist again via VELCRO™ straps, to provide collapsible support for a strained wrist. As noted previously, the present invention also contemplates using support members (10) of various dimensions to provide therapeutic support for different joints, such as, for example, the collapsible support member (10) and positioning means (20) for the knee joint illustrated in FIG. 5.

The collapsible tactile support of the present invention is particularly useful for therapeutic purposes, since it can provide support for the injured joint while at the same time allowing for rehabilitative movement in the joint without any need to remove the support itself. In fact, the ability of the present invention to return to its original configuration when the collapsing pressure is removed actually aids in the therapeutic movement. Thus, an outside force or pressure can be applied (i.e. by the non-injured hand) to the injured joint in excess of the collapse threshold of the support member (10), in order to bend the support member (10) and allow for rehabilitative movement in the joint itself. Then, when the outside force is removed the injured joint is returned to its original supported condition via the return action of the support member (10).

The present invention has been described in terms of the preferred embodiment. One skilled in the art will recognize that it would be possible to construct the elements of the present invention from a variety of materials and to modify the placement of the components in a variety of ways. While the preferred embodiments have been described in detail and shown in the accompanying drawings, it will be evident that various further modifications are possible without departing from the scope of the invention as set forth in the following claims.

I claim:

1. A collapsible support providing corrective tension to a joint, comprising:
   a) a means for supporting a joint and for collapsing to permit unrestrained joint movement and provide a tactile signal when a predetermined threshold level of force is exceeded and for automatically returning to its original configuration when said force is reduced below said threshold; and
   b) a means for positioning said means for supporting against said joint.

2. The support of claim 1, wherein said means for supporting comprises a support strip and a cover.

3. The support of claim 1, wherein said means for supporting comprises a spring steel type strip slightly curved about a longitudinal axis.

4. The support of claim 1, wherein said means for supporting comprises a padded support strip and a cover.

5. The support of claim 1, wherein said means for positioning comprises at least one measurably adjustable strap and tightening means.

6. The support of claim 1, wherein said means for positioning comprises a thumb harness.

7. The support of claim 1, wherein said means for positioning comprises a finger harness.

8. A sports training device kit for aiding users of many different skill levels in maintaining correct joint position, said kit comprising:
   a) a plurality of collapsible support members, each support member having at least one dimension which is different from every other support member for selectively providing the user with a plurality of collapsible support members each of which has a different predetermined collapse threshold; and b) a means for positioning at least one of said support members over the bending point of a user's joint.

9. The sports training device kit of claim 8, wherein said bending of said user's joint flexes said collapsible support member when said collapse threshold is exceeded, to permit unrestrained joint movement and provide a tactile signal.

10. The sports training device kit of claim 8, wherein said support member further comprises a support strip and a cover.

11. The sports training device kit of claim 8, wherein said support member comprises a spring steel strip having a first end and a second end and slightly curved about a longitudinal axis to form a concave side and a convex side, said strip characterized by its ability to collapse to permit substantially unrestrained movement of the joint and to generate a tactile signal when a center portion of the strip is anchored and a predetermined amount of pressure is applied against either end of the concave side, and to return automatically to its original position when said pressure is reduced below said predetermined amount.

12. The sports training device kit of claim 8, wherein said support member further comprises a padded support strip and a cover.

13. The sports training kit of claim 8, further comprising a block adapted to be positioned between said support member and the joint to allow limited movement of said joint prior to engagement with said support member.

14. The sports training device kit of claim 8, wherein said support member is adapted to be positioned over a wrist joint.

15. The sports training device kit of claim 14, wherein said means for positioning comprises at least one strap and tightening means.

16. The sports training device kit of claim 14, wherein said means for positioning comprises a thumb harness.

17. The sports training device kit of claim 14, wherein said means for positioning comprises a finger harness.

18. The sports training device kit of claim 14, wherein said means for positioning comprises a glove having a slip pocket for insertion of said support member.

19. The sports training device kit of claim 14, wherein said slip pocket further comprises a tightening means.

20. A golf training aid to control the cocking of a user's wrist in relation to the back surface of the user's hand and forearm, comprising; a support means for assisting the user in maintaining the back surface of the user's hand in a substantially coplanar arrangement with the back surface of the user's forearm, for flexing when a force applied by movement of the user's hand exceeds a predetermined collapse threshold, thereby allowing substantially unrestrained wrist movement, for providing a tactile signal to the user when said threshold has been exceeded, and for returning to its original configuration when said force falls below said threshold; and, at least one adjustable strap for positioning and tightening said support means over a bending point of the user's wrist.

21. A golf training aid to assist a user in controlling the position of a user's wrist, hand and forearm, comprising:

a collapsible, elongated spring steel type strip means having a first end and a second end, said strip being curved in a direction perpendicular to a longitudinal axis passing along said strip from said first end to said second end forming, in cross-section perpendicular to said longitudinal axis, a generally concave first side and a generally convex second side, said strip means for supporting the position of user's wrist in relation to the hand and forearm, for collapsing and generating a tactile signal when a center portion of the strip is anchored and a predetermined amount of pressure is applied against either end of the concave side, and for returning to the original configuration when said pressure is reduced below said predetermined amount;

a sleeve for receiving the collapsible strip means, said sleeve including a means for positioning the sleeve over the user's wrist with the concave side facing a portion of the user's wrist, with the first end resting on a portion of the user's hand adjacent to the wrist, and with the second end resting on a portion of the user's forearm adjacent to the wrist.

* * * * *